United States Patent
Dhuppad et al.

(10) Patent No.: US 10,555,903 B2
(45) Date of Patent: Feb. 11, 2020

(54) NEBULIZABLE COMPOSITIONS OF TIOTROPIUM AND FORMOTEROL

(71) Applicant: GLENMARK SPECIALTY S.A., La Chaux-de-Fonds (CH)

(72) Inventors: Ulhas R. Dhuppad, Nashik (IN); Ramprasad Murugan, Dharmapuri Dist. (IN); Mahadeorao S. Rase, Maharashtra (IN); Franciscus Koppenhagen, Deerfield Beach, FL (US); Julianne Berry, Westfield, NJ (US)

(73) Assignee: GLENMARK SPECIALTY S.A., La Chaux-de-Fonds (CH)

( * ) Notice: Subject to any disclaimer, the term of this patent is extended or adjusted under 35 U.S.C. 154(b) by 0 days.

(21) Appl. No.: 15/783,146

(22) Filed: Oct. 13, 2017

(65) Prior Publication Data

US 2018/0104184 A1 Apr. 19, 2018

(30) Foreign Application Priority Data

Oct. 14, 2016 (IN) .............................. 201621035197

(51) Int. Cl.

| | |
|---|---|
| A61K 9/00 | (2006.01) |
| B65D 81/32 | (2006.01) |
| A61K 45/06 | (2006.01) |
| A61M 15/00 | (2006.01) |
| A61K 31/167 | (2006.01) |
| A61K 31/46 | (2006.01) |
| A61K 47/02 | (2006.01) |
| A61K 47/12 | (2006.01) |
| A61K 47/18 | (2017.01) |
| A61M 11/00 | (2006.01) |

(52) U.S. Cl.
CPC .......... *A61K 9/0078* (2013.01); *A61K 31/167* (2013.01); *A61K 31/46* (2013.01); *A61K 45/06* (2013.01); *A61K 47/02* (2013.01); *A61K 47/12* (2013.01); *A61K 47/183* (2013.01); *A61M 15/0028* (2013.01); *A61M 15/0031* (2014.02); *B65D 81/32* (2013.01); *A61M 11/003* (2014.02); *A61M 11/005* (2013.01)

(58) Field of Classification Search
CPC ...... A61K 31/167; A61K 31/46; A61K 45/06; A61K 47/02; A61K 47/12; A61K 47/183; A61K 9/0078; A61M 15/0028; A61M 15/0031; B65D 81/32; A61P 11/00; A61P 11/08

See application file for complete search history.

(56) References Cited

U.S. PATENT DOCUMENTS

| | | | |
|---|---|---|---|
| 6,433,027 B1 | 8/2002 | Bozung et al. | |
| 6,475,467 B1* | 11/2002 | Keller | A61K 9/008 424/45 |
| 6,481,435 B2* | 11/2002 | Hochrainer | A61K 9/0078 128/200.14 |
| 6,537,524 B1 | 3/2003 | Hassan et al. | |
| 6,667,344 B2* | 12/2003 | Banerjee | A61K 9/0078 424/45 |
| 6,777,423 B2 | 8/2004 | Banholzer et al. | |
| RE39,820 E | 9/2007 | Banholzer et al. | |
| 8,697,719 B2* | 4/2014 | Gore | C07D 491/18 514/291 |
| 9,757,365 B2* | 9/2017 | Dhuppad | A61K 9/0078 |
| 9,987,260 B2* | 6/2018 | Dhuppad | A61P 11/08 |
| 2007/0098644 A1* | 5/2007 | Ray, II | A61K 9/0073 424/45 |
| 2007/0293460 A1* | 12/2007 | Ray, II | A61K 9/0073 514/171 |
| 2010/0330186 A1* | 12/2010 | Meade | A61K 9/0075 424/489 |
| 2014/0224815 A1 | 8/2014 | Gallem et al. | |

FOREIGN PATENT DOCUMENTS

WO WO-03035030 A1 5/2003

OTHER PUBLICATIONS

Tashkin et al., "Concomitant treatment with nebulized formoterol and tiotropium in subjects with COPD: A placebo-controlled trial", 2008, Respiratory Medicine, 102(4), pp. 479-487. (Year: 2008).*
Hugh Smyth, 2006, "Excipients for Pulmonary Formulations", In Katdare, A., & Chaubal, M. (Eds.), Excipient Development for Pharmaceutical, Biotechnology, and Drug Delivery Systems, (pp. 225-249) CRC Press. (Year: 2006).*
International Search Report issued in PCT/IB2017/056371 dated Jan. 5. 2018.
Prescribing information for Spiriva Respimat (Jun. 9, 2016).
Prescribing information for Perforomist (Jan. 11, 2012).

* cited by examiner

Primary Examiner — My-Chau T. Tran

(74) Attorney, Agent, or Firm — Blank Rome LLP

(57) ABSTRACT

The present disclosure relates to a nebulization composition comprising tiotropium and formoterol for the treatment of inflammatory or obstructive airway disease. The present disclosure also relates to a process for preparing the composition.

30 Claims, No Drawings

NEBULIZABLE COMPOSITIONS OF TIOTROPIUM AND FORMOTEROL

This patent application claims priority to Indian Provisional Patent Application No. 201621035197, filed on Oct. 14, 2016, the entire contents of which are incorporated by reference herein.

FIELD OF THE INVENTION

The present invention relates to nebulization compositions of tiotropium or a pharmaceutically acceptable salt thereof and formoterol or a pharmaceutically acceptable salt thereof, their use in the treatment of inflammatory and/or obstructive airway diseases, and processes for preparing them.

BACKGROUND OF THE INVENTION

Respiratory disorders include a number of airway diseases. Asthma and chronic obstructive pulmonary disease (COPD) are among the most prevalent and life threatening conditions.

COPD is a chronic disorder that is characterized by loss of elasticity of the airways and air sacs, destruction of alveolar walls, inflammation of airways, and high mucus production in the airways. All of these effects lead to clogging of the airways making it difficult for the patient to breathe. Asthma is a chronic disease involving airways of the lung that is characterized by coughing, wheezing, and shortness of breath.

Tiotropium bromide is approved in the U.S. under the brand name Spiriva Respimat® as a propellant free metered dose inhaler.

Formoterol fumarate is approved in the U.S. as an inhalation solution under the brand name Perforomist®.

U.S. Pat. No. 6,537,524 discloses a medicament containing, separately or together, (A) formoterol or a pharmaceutically acceptable salt thereof and (B) a tiotropium salt of a pharmaceutically acceptable acid, for simultaneous, sequential or separate administration.

SUMMARY OF THE INVENTION

One embodiment of the present invention is a dual chamber container in which one chamber contains a nebulizable tiotropium composition and the other chamber contains a nebulizable formoterol composition. The two drugs are intended to be combined together before or at the time of administration to a patient.

The nebulizable tiotropium composition contains tiotropium or a pharmaceutically acceptable salt thereof, such as tiotropium bromide (e.g., tiotropium bromide monohydrate or anhydrous tiotropium bromide). The nebulizable tiotropium composition is preferably an aqueous solution in which the tiotropium or pharmaceutically acceptable salt thereof is dissolved. In one embodiment, the nebulizable tiotropium composition includes an isotonicity agent (e.g., sodium chloride), a pH adjusting agent (e.g., hydrochloric acid, sodium hydroxide, or a combination thereof), optionally a complexing agent (e.g., edetate disodium), or any combination of any of the foregoing. The nebulizable composition is substantially free of preservative.

The nebulizable formoterol composition contains formoterol or a pharmaceutically acceptable salt thereof, such as formoterol fumarate (e.g., formoterol fumarate dihydrate). The nebulizable formoterol composition is preferably an aqueous solution in which the formoterol or pharmaceutically acceptable salt thereof is dissolved. In one embodiment, the nebulizable formoterol composition includes an isotonicity agent (e.g., sodium chloride), a pH adjusting agent (e.g., hydrochloric acid, sodium hydroxide, or a combination thereof), optionally a complexing agent (e.g., edetate disodium), a buffer (e.g., sodium citrate), or any combination of any of the foregoing. The nebulizable composition is substantially free of preservative.

Another embodiment is a nebulizable tiotropium-formoterol composition comprising a combination of tiotropium or a pharmaceutically acceptable salt thereof and formoterol or a pharmaceutically acceptable salt thereof. The nebulizable tiotropium-formoterol composition is preferably an aqueous solution in which the formoterol or pharmaceutically acceptable salt thereof and tiotropium or pharmaceutically acceptable salt thereof are dissolved. In one embodiment, the nebulizable tiotropium-formoterol composition includes an isotonicity agent (e.g., sodium chloride), a pH adjusting agent (e.g., hydrochloric acid, sodium hydroxide, or a combination thereof), a complexing agent (e.g., edetate disodium), a buffer (e.g., sodium citrate), or any combination of any of the foregoing. The nebulizable composition may be a sterile, unit dose composition, and may be in a single chamber container.

In yet another embodiment, the nebulizable tiotropium-formoterol composition comprises tiotropium or a pharmaceutically acceptable salt thereof (e.g., tiotropium bromide), formoterol or a pharmaceutically acceptable salt thereof (e.g., formoterol fumarate), a pH adjusting agent, and an isotonicity agent. The nebulizable composition may optionally further include a complexing agent, a buffer, a pharmaceutically acceptable vehicle, or any combination thereof. The nebulizable composition is substantially free of preservative.

Yet another embodiment is the use of a dual chamber container containing both a nebulizable tiotropium composition and a nebulizable formoterol composition for the treatment of an inflammatory or obstructive airway disease, such as asthma or COPD.

Yet another embodiment is the use of a dual chamber container described herein containing both a nebulizable tiotropium composition and a nebulizable formoterol composition for the treatment of an inflammatory or obstructive airway disease, such as asthma or COPD.

In yet another embodiment, the nebulizable composition(s) described herein are storage stable. For example, in one embodiment, the nebulizable composition(s) described herein contain greater than about 80%, 90%, 95%, 98%, or 99% of the initial amount of tiotropium and/or formoterol (or salts thereof) after storage for 1 month, 3 months, or 6 months at about 2-8° C. In another embodiment, the nebulizable composition(s) described herein contain greater than about 80%, 90%, 95%, 98%, or 99% of the initial amount of tiotropium and/or formoterol (or salts thereof) after storage for 1 month, 3 months, or 6 months at about 25° C. and 60% relative humidity. In yet another embodiment, the nebulizable composition(s) described herein contain greater than about 80%, 90%, 95%, 98%, or 99% of the initial amount of tiotropium and/or formoterol (or salts thereof) after storage for 1 month, 3 months, or 6 months at about 40° C. and 75% relative humidity.

Yet another embodiment is one or more prefilled containers containing a nebulizable composition (such as the nebulizable tiotropium-formoterol composition) according to any of the embodiments described herein.

Yet another embodiment is a kit comprising a nebulizer and a dual chamber container as described herein.

Yet another embodiment is a kit comprising a nebulizer, a nebulizable tiotropium composition as described herein, and a nebulizable formoterol composition as described herein.

Yet another embodiment is a kit comprising a nebulizer and a nebulizable tiotropium-formoterol composition as described herein.

Yet another embodiment is a method of treating an inflammatory or obstructive airway disease (such as COPD or asthma) in a patient in need thereof by administering to the patient the nebulizable tiotropium composition and the nebulizable formoterol composition described herein. The nebulizable tiotropium composition and the nebulizable formoterol composition are/may be combined prior to being inhaled by the patient. The nebulizable tiotropium composition and the nebulizable formoterol composition may be administered from the dual chamber container described herein. Preferably, a therapeutically effective amount of tiotropium (or a pharmaceutically acceptable salt thereof, preferably tiotropium bromide) and formoterol (or a pharmaceutically acceptable salt thereof, preferably formoterol fumarate) are administered.

Other objects, features and advantages of the present invention will be apparent to those of ordinary skill in the art in view of the following detailed description of the invention and claims.

DETAILED DESCRIPTION OF THE INVENTION

Respiratory diseases such as asthma and COPD are prevalent and can be life threatening. Dosage forms for the treatment of asthma and COPD include metered dose inhalation and dry powder inhalation. Drug delivery via metered dose inhalation and dry powder inhalation require synchronization with the patient's breathing pattern and the device characteristics. This often requires the patient to be trained with the device. In contrast, nebulization does not require the patient to undergo cumbersome training. With nebulization, the patient need not synchronize his or her breathing patterns with the device, and the delivery of the drug is independent of the breathing pattern of the patient. This is especially convenient for pediatric and geriatric patients. Nebulized drugs are deposited directly into the respiratory tract, thereby allowing higher drug concentrations to be achieved in the bronchial tree and pulmonary bed with fewer adverse effects.

Tiotropium

Tiotropium is an anticholinergic agent with specificity for muscarinic receptors. Tiotropium is chemically described as (1α, 2β, 4β, 5α, 7β)-7-[(hydroxydi-2-thienylacetyl)oxy]-9,9-dimethyl-3-oxa-9-zoniatricyclo[3.3.1.0²,⁴] nonane. It is a synthetic, non-chiral, quaternary ammonium compound having the molecular formula $C_{19}H_{22}NO_4S_2$ and the following structure:

As used herein, the term "tiotropium", unless otherwise indicated, includes, but is not limited to, tiotropium in any physical form such as the amorphous form and crystalline forms (e.g., anhydrous, hydrate, and other solvate forms). 2-hydroxy-2,2-dithiophen-2-ylacetic acid may be an impurity of tiotropium, referred to herein as "Impurity A." Salts of tiotropium include, but are not limited to, acid addition salts and base salts thereof. Suitable salts of tiotropium include, but are not limited to, halide salts such as bromide, chloride and iodide salts. These and other salts are described, for example, in U.S. Pat. No. RE 39,820, which is hereby incorporated by reference in its entirety. The preparation of tiotropium bromide monohydrate is described in U.S. Pat. No. 6,777,423, which is incorporated herein by reference in its entirety. One preferred salt of tiotropium for the nebulizable compositions described herein is tiotropium bromide. Tiotropium bromide may be in the form of its monohydrate salt (tiotropium bromide monohydrate), anhydrous salt, amorphous monohydrate salt or as an anhydrous amorphous salt.

Formoterol

Formoterol is a long-acting, beta 2-adrenergic receptor agonist. It is chemically described as (±)-2-hydroxy-5-[(1RS)-1-hydroxy-2-[[(1RS)-2-(4-methoxyphenyl)-1-methylethyl]amino]-ethyl]formanilide. Formoterol has the molecular formula $C_{19}H_{24}N_2O_4$ and the following structure:

As used herein, the term "formoterol", unless otherwise indicated, includes, but is not limited to, formoterol in any physical form such as the amorphous form and crystalline forms (e.g., anhydrous, hydrate, and other solvate forms). Salts of formoterol include, but are not limited to, acid addition salts and base salts thereof. Suitable salts of formoterol include, but are not limited to, salts of mineral acids, such as hydrochlorides and sulfates, and salts of organic acids, such as acetates, lactates, malates, tartrates, citrates, ascorbates, succinates, butyrates, valerates and fumarates. One preferred salt of formoterol for the nebulizable compositions described herein is formoterol fumarate, such as in the form of its dihydrate salt (formoterol fumarate dihydrate).

Combination

The weight ratio of tiotropium (or pharmaceutically acceptable salt thereof) to formoterol (or pharmaceutically acceptable salt thereof) in the dual chamber container or in the single nebulizable composition containing both the tiotropium and formoterol can be from about 1:256 to about 256:1 (on the equivalent weight of tiotropium free base and formoterol free base).

Nebulizable Tiotropium Composition

The nebulizable tiotropium composition includes tiotropium or a pharmaceutically acceptable salt thereof and one or more pharmaceutically acceptable excipients. The nebulizable tiotropium composition preferably is an aqueous solution in which the tiotropium or a pharmaceutically acceptable salt thereof (e.g., tiotropium bromide) is dissolved.

In one embodiment, the amount of tiotropium or its salt (e.g., tiotropium bromide) in the nebulizable tiotropium composition is about 0.00125 mg to about 0.64 mg (based on the equivalent amount of tiotropium free base). Preferably, the composition contains tiotropium bromide in an amount of about 0.00125 mg, 0.0025 mg, 0.005 mg, 0.01 mg, 0.02 mg, 0.04 mg, 0.08 mg, 0.16 mg, 0.32 mg or 0.64 mg (based on the equivalent amount of tiotropium free base). In one embodiment, the composition contains about 0.000125% w/v to about 0.064% w/v of tiotropium bromide, such as about 0.000125%, 0.00025%, 0.0005%, 0.001%, 0.002%, 0.004%, 0.008%, 0.016%, 0.032% or 0.064% w/v.

In another embodiment, the amount of tiotropium or its salt (e.g., tiotropium bromide) in the nebulizable tiotropium composition is from about 1 µg to about 100 µg or from about 10 µg to about 80 µg, for example, about 5 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg (based on the equivalent amount of tiotropium free base).

Suitable pharmaceutically acceptable excipients which may be incorporated in the nebulizable tiotropium composition include, but are not limited to, isotonicity agents, pH adjusting agents, complexing agents, buffers, surfactants, anti-oxidants, and pharmaceutically acceptable vehicles.

The isotonicity agent may be an ionic salt. Suitable isotonicity agents include, but are not limited to, ammonium carbonate, ammonium chloride, ammonium lactate, ammonium nitrate, ammonium phosphate, ammonium sulfate, ascorbic acid, bismuth sodium tartrate, boric acid, calcium chloride, calcium disodium edetate, calcium gluconate, calcium lactate, citric acid, dextrose, diethanolamine, dimethyl sulfoxide, edetate disodium, edetate trisodium monohydrate, fluorescein sodium, fructose, galactose, glycerin, lactic acid, lactose, magnesium chloride, magnesium sulfate, mannitol, polyethylene glycol, potassium acetate, potassium chlorate, potassium chloride, potassium iodide, potassium nitrate, potassium phosphate, potassium sulfate, propylene glycol, silver nitrate, sodium acetate, sodium bicarbonate, sodium biphosphate, sodium bisulfite, sodium borate, sodium bromide, sodium cacodylate, sodium carbonate, sodium chloride, sodium citrate, sodium iodide, sodium lactate, sodium metabisulfite, sodium nitrate, sodium nitrite, sodium phosphate, sodium propionate, sodium succinate, sodium sulfate, sodium sulfite, sodium tartrate, sodium thiosulfate, sorbitol, sucrose, tartaric acid, triethanolamine, urea, urethane, uridine, zinc sulfate, and any combination of any of the foregoing. Suitable osmotic adjusting agents include, but are not limited to, sodium chloride, potassium chloride, zinc chloride, calcium chloride and any combination of any of the foregoing. Other osmotic adjusting agents include, but are not limited to, mannitol, glycerol, dextrose and any combination of any of the foregoing. A preferred isotonicity agent is sodium chloride. The amount of isotonicity agent may range from about 0.0001% w/v to about 264% w/v. The osmolality of the nebulizable tiotropium composition may be from about 200-500 mOsm/kg.

Suitable pH adjusting agents include, but are not limited to, pharmaceutically acceptable acids. Non-limiting examples of suitable pharmaceutically acceptable acids include inorganic acids, such as hydrochloric acid, hydrobromic acid, nitric acid, sulfuric acid, and phosphoric acid, and any combination of any of the foregoing. Non-limiting examples of other suitable pharmacologically acceptable acids include organic acids, such as ascorbic acid, citric acid, malic acid, maleic acid, tartaric acid, succinic acid, fumaric acid, acetic acid, formic acid, propionic acid, and any combination of any of the foregoing. The pH adjusting agents may be selected from one or more organic acids selected from ascorbic acid, fumaric acid and citric acid. A preferred organic acid is citric acid. Mixtures of the above-mentioned acids may also be used, particularly in the case of acids which have other properties in addition to their acidifying properties, e.g., those which act as flavorings or antioxidants, such as citric acid or ascorbic acid.

Suitable complexing agents include, but are not limited to, EDTA and salts thereof, such as edetate disodium. The nebulizable tiotropium composition may contain about 0.01% complexing agent, about 0.02% complexing agent, about 0.03% complexing agent, about 0.04% complexing agent, about 0.05% complexing agent, about 0.06% complexing agent, about 0.07% complexing agent, about 0.08% complexing agent, about 0.09% complexing agent, or about 0.1% complexing agent. The nebulizable tiotropium composition may contain about 0.1 mg/mL complexing agent, about 0.2 mg/mL complexing agent, about 0.3 mg/mL complexing agent, about 0.4 mg/mL complexing agent, about 0.5 mg/mL complexing agent, about 0.6 mg/mL complexing agent, about 0.7 mg/mL complexing agent, about 0.8 mg/mL complexing agent, about 0.9 mg/mL complexing agent, or about 1.0 mg/mL complexing agent.

In certain embodiments, the complexing agent (such as EDTA or edetate disodium) may be present in the nebulizable tiotropium composition at a concentration of less than about 0.1% by weight, such as less than about 0.09%, less than about 0.08%, less than about 0.07%, less than about 0.06%, less than about 0.05%, less than about 0.04%, less than about 0.03%, less than about 0.02%, or less than about 0.01% by weight. In another embodiment, the complexing agent (such as EDTA or edetate disodium) may be present in the nebulizable tiotropium composition at a less than about 1.0 mg/mL, such as less than about 0.9 mg/mL, less than about 0.8 mg/mL, less than about 0.7 mg/mL, less than about 0.6 mg/mL, less than about 0.5 mg/mL, less than about 0.4 mg/mL, less than about 0.3 mg/mL, less than about 0.2 mg/mL, or less than about 0.1 mg/mL.

The nebulizable tiotropium composition may contain about 0.01% edetate disodium, about 0.02% edetate disodium, about 0.03% edetate disodium, about 0.04% edetate disodium, about 0.05% edetate disodium, about 0.06% edetate disodium, about 0.07% edetate disodium, about 0.08% edetate disodium, about 0.09% edetate disodium, or about 0.1% edetate disodium by weight. In one preferred embodiment, the nebulizable tiotropium composition contains about 0.05% edetate sodium by weight. The nebulizable tiotropium composition may contain about 0.1 mg/mL edetate disodium, about 0.2 mg/mL edetate disodium, about 0.3 mg/mL edetate disodium, about 0.4 mg/mL edetate disodium, about 0.5 mg/mL edetate disodium, about 0.6 mg/mL edetate disodium, about 0.7 mg/mL edetate disodium, about 0.8 mg/mL edetate disodium, about 0.9 mg/mL edetate disodium, or about 1.0 mg/mL edetate disodium by weight. In one preferred embodiment, the nebulizable tiotropium composition contains about 0.5 mg/mL edetate sodium.

Suitable buffers in the pH range of about 2.0 to about 8.0 include, but are not limited to, acetate, barbital, borate, Britton-Robinson, cacodylate, citrate (e.g., sodium citrate), collidine, formate, maleate, McIlvaine, phosphate, Prideaux-Ward, succinate, citrate-phosphate-borate (Teorell-Stanhagen), veronal acetate, MES, BIS-TRIS, ADA, ACES, PIPES, MOPSO, BIS-TRIS PROPANE, BES, MOPS, TES, HEPES, DIPSO, MOBS, TAPSO, TRIZMA, HEPPSO, POPSO, TEA, EPPS, TRICINE, GLY-GLY, BICINE, HEPBS, TAPS, and AMPD buffers, and any combination of the foregoing. The nebulizable tiotropium composition may contain sodium citrate, for example, at a concentration of about 0.0001% w/v to about 2.20% w/v, and citric acid, for example, at a concentration of about 0.0001% w/v to about 0.53% w/v, to control pH.

Suitable surfactants include, but are not limited to, $C_{5-20}$-fatty alcohols, $C_{5-20}$-fatty acids, $C_{5-20}$-fatty acid esters, lecithin, glycerides, propylene glycol esters, polyoxyethylenes, polysorbates, sorbitan esters, carbohydrates, and any combination of any of the foregoing. $C_{5-20}$-fatty acids, propylene glycol diesters of the $C_{5-20}$-fatty acids, triglycerides of the $C_{5-20}$-fatty acids, and sorbitans of the $C_{5-20}$-fatty acids are preferred. In one preferred embodiment, the surfactant is selected from oleic acid, sorbitan mono-, di- or tri-oleates, and any combination of any of the foregoing.

Suitable antioxidants include, but are not limited to, ascorbic acid, vitamin A, vitamin E, tocopherols, and any combination of any of the foregoing.

Suitable pharmaceutically acceptable vehicles include, but are not limited to, water alone or in combination with one or more co-solvents. Any co-solvent that is suitable for inhalation and capable of dissolving or solubilizing the tiotropium in the mixture of co-solvent and water can be used. Examples of suitable co-solvents include, but are not limited to, alcohols, ethers, hydrocarbons, and perfluorocarbons. Preferably, the co-solvent is a short chain polar alcohol. More preferably, the co-solvent is an aliphatic alcohol having from one to six carbon atoms, such as ethanol or isopropanol. A preferred co-solvent is ethanol. Non-limiting examples of suitable hydrocarbons include n-butane, isobutane, pentane, neopentane and isopentanes. Non-limiting examples of suitable ethers include dimethyl ether and diethyl ether. Non-limiting examples of suitable perfluorocarbons include perfluoropropane, perfluorobutane, perfluorocyclobutane, and perfluoropentane.

In certain embodiments, the pH of the tiotropium nebulizable composition may be from about 2.0 to about 6.0, preferably from about 2.0 to about 4.5, more preferably from about 2.5 to about 3.5, e.g., from about 2.5 to about 3.0. The tiotropium nebulizable composition may have a pH of about 2.5, about 2.6, about 2.7, about 2.8, about 2.9, about 3.0, about 3.1, about 3.2, about 3.3, about 3.4, or about 3.5. In one preferred embodiment, the pH is about 2.7.

In one embodiment, the nebulizable tiotropium composition includes a pH adjusting agent, an isotonicity agent, and a pharmaceutically acceptable vehicle. For example, the nebulizable tiotropium composition may include, in addition to the tiotropium or salt thereof (such as tiotropium bromide), (i) hydrochloric acid or citric acid, (ii) sodium chloride, and (iii) water. In one embodiment, nebulizable tiotropium composition includes (i) hydrochloric acid or citric acid, (ii) about 9 mg/mL sodium chloride, and (iii) water.

In another embodiment, the nebulizable tiotropium composition includes a pH adjusting agent, an isotonicity agent, a pharmaceutically acceptable vehicle, and a complexing agent. For example, the nebulizable tiotropium composition may include, in addition to the tiotropium or salt thereof (such as tiotropium bromide), (i) hydrochloric acid or citric acid, (ii) sodium chloride, (iii) water, and (iv) edetate disodium. In one embodiment, nebulizable tiotropium composition includes (i) hydrochloric acid or citric acid, (ii) about 9 mg/mL sodium chloride, (iii) water, and (iv) edetate disodium (e.g., about 0.01 to about 0.5 mg/mL, such as about 0.2 mg/mL or about 0.5 mg/mL). Yet another embodiment is a nebulizable tiotropium composition comprising, in addition to tiotropium bromide (e.g., 10, 15, 20, 25, 30, 35, or 40 mcg of tiotropium bromide (on the equivalent to tiotropium free base)), (i) citric acid, (ii) about 9 mg/mL sodium chloride, (iii) water, and (iv) about 0.5 mg/mL edetate disodium, where the pH of the composition is from about 2.5 to about 3.0, such as about 2.7. In yet another embodiment is a nebulizable tiotropium composition comprising, in addition to tiotropium bromide (e.g., 10, 15, 20, 25, 30, 35, or 40 mcg of tiotropium bromide (on the equivalent to tiotropium free base)), (i) about 0.76 mg/mL citric acid, (ii) about 9 mg/mL sodium chloride, (iii) water, and (iv) about 0.5 mg/mL edetate disodium, where the pH of the composition is from about 2.5 to about 3.0, such as about 2.7.

In one embodiment, the nebulizable tiotropium composition is free or substantially free of a preservative (such as a benzalkonium salt, e.g., benzalkonium chloride). The term "substantially free of preservative" or "substantially preservative free" denotes that a preservative is not present in the composition in an amount sufficient to materially act as a preservative for the nebulizable composition. In one embodiment, the preservative may be present in a concentration less than 0.008% w/w based on total weight of the composition. Generally, nebulizable compositions contain a preservative such as benzalkonium chloride. A common problem with the use of benzalkonium chloride is that it may cause paradoxic bronchoconstriction if the solution is administered repeatedly over short intervals, and frequent exposure to benzalkonium chloride may lead to occupational asthma. Another problem is that when inhaled by patients, the benzalkonium chloride can cause dose-dependent bronchoconstriction. The nebulizable compositions described herein may be provided without benzalkonium chloride, thereby making them suitable for repeated administration over a short period of time. Also, administering a substantially benzalkonium chloride-free nebulizable composition to a patient reduces the concomitant liability of adverse effects associated with benzalkonium chloride alone or in combination with other excipients and/or the active agents. It also negates the toxicity and other side effects associated with benzalkonium chloride.

In another embodiment, the nebulizable tiotropium composition is free or substantially free of a complexing agent, such as ethylene diamine tetra-acetic acid (EDTA) or a salt thereof. For example, the nebulizable tiotropium composition may contain less than 0.1% of a complexing agent such as ethylene diamine tetra-acetic acid (EDTA) or a salt thereof, such as less than about 0.05%, less than about 0.02%, less than about 0.01%, or less than about 0.008%, based on total weight of nebulizable tiotropium composition.

In yet another embodiment, the nebulizable tiotropium composition is free or substantially free of both (a) a complexing agent, such as ethylene diamine tetra-acetic acid (EDTA) or a salt thereof, and (b) a preservative, such as a benzalkonium salt, e.g., benzalkonium chloride. For example, the nebulizable tiotropium composition may contain less than 0.001% of a complexing agent such as ethylene diamine tetra-acetic acid (EDTA) or a salt thereof and less than 0.001% of a complexing agent, such as ethylene diamine tetra-acetic acid (EDTA) or a salt thereof.

Nebulizable Formoterol Composition

The nebulizable formoterol composition includes formoterol or a pharmaceutically acceptable salt thereof and one or more pharmaceutically acceptable excipients. The nebulizable formoterol composition preferably is an aqueous solution in which the formoterol or a pharmaceutically acceptable salt thereof (e.g., formoterol fumarate, such as formoterol fumarate dihydrate) is dissolved.

In one embodiment, the amount of formoterol or its salt (e.g., formoterol fumarate or formoterol fumarate dihydrate) in the nebulizable formoterol composition is about 0.0025 mg to about 0.32 mg (based on the equivalent amount of formoterol free base). Preferably, the composition contains formoterol fumarate in amounts of about 0.0025 mg, 0.005 mg, 0.01 mg, 0.02 mg, 0.04 mg, 0.08 mg, 0.16 mg, or 0.32 mg (based on the equivalent amount of formoterol free base). In one embodiment, the composition contains about 0.00025% w/v to about 0.032% w/v of formoterol fumarate, such as about 0.00025%, 0.0005%, 0.001%, 0.002%, 0.004%, 0.008%, 0.016%, or 0.032% w/v.

In another embodiment, the amount of formoterol or its salt (e.g., formoterol fumarate) in the nebulizable formoterol composition is from about 1 µg to about 100 µg or from about 10 µg to about 80 µg, for example, about 5 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, or about 100 µg (based on the equivalent amount of formoterol free base).

Suitable pharmaceutically acceptable excipients which may be incorporated in the nebulizable formoterol composition include, but are not limited to, isotonicity agents, pH adjusting agents, complexing agents, buffers, surfactants, anti-oxidants, and pharmaceutically acceptable vehicles. The specific excipients and their amounts disclosed above also apply to the nebulizable formoterol composition.

In one embodiment, the isotonicity agent may be sodium chloride. The nebulizable formoterol compositions may contain about 2-10 mg/ml sodium chloride, such as about 2 mg/ml, about 3 mg/ml, about 4 mg/ml, about 5 mg/ml, about 6 mg/ml, about 7 mg/ml, about 8 mg/ml, about 9 mg/ml or about 10 mg/ml of sodium chloride.

In certain embodiments, the pH of the nebulizable formoterol composition may be from about 4.5 to about 6.5, more preferably from about 5.0 to about 6.0. The nebulizable formoterol composition may have a pH of about 5.0, about 5.1, about 5.2, about 5.3, about 5.4, about 5.5, about 5.6, about 5.7, about 5.8, about 5.9, or about 6.0. In one preferred embodiment, the pH is about 5.5.

In one embodiment, the nebulizable formoterol composition includes a pH adjusting agent, an isotonicity agent, and a pharmaceutically acceptable vehicle. For example, the nebulizable tiotropium composition may include, in addition to the formoterol or salt thereof (such as formoterol fumarate), (i) hydrochloric acid or citric acid, (ii) sodium chloride, and (iii) water. In one embodiment, nebulizable formoterol composition includes (i) hydrochloric acid or citric acid, (ii) about 9 mg/mL sodium chloride, and (iii) water.

In another embodiment, the nebulizable formoterol composition includes a pH adjusting agent, an isotonicity agent, a pharmaceutically acceptable vehicle, and a complexing agent. For example, the nebulizable formoterol composition may include, in addition to the formoterol or salt thereof (such as formoterol fumarate), (i) hydrochloric acid or citric acid, (ii) sodium chloride, (iii) water, and (iv) edetate disodium. In one embodiment, nebulizable formoterol composition includes (i) hydrochloric acid or citric acid, (ii) about 5 mg/mL sodium chloride, (iii) water, and (iv) edetate disodium (e.g., about 0.01 to about 0.5 mg/mL, such as about 0.2 mg/mL or about 0.5 mg/mL). Yet another embodiment is a nebulizable formoterol composition may include, in addition to the formoterol or salt thereof (such as formoterol fumarate), (i) hydrochloric acid or citric acid, (ii) sodium chloride, (iii) water, (iv) edetate disodium, and (v) sodium citrate. In one embodiment, nebulizable formoterol composition includes, in addition to formoterol fumarate, (i) hydrochloric acid or citric acid (e.g., citric acid anhydrous), (ii) about 5 mg/mL sodium chloride, (iii) water, (iv) edetate disodium (e.g., about 0.01 to about 0.5 mg/mL, such as about 0.2 mg/mL or about 0.5 mg/mL), and (v) sodium citrate (e.g., sodium citrate dihydrate) (such as 13.2 mg/mL).

Yet another embodiment is a nebulizable formoterol composition comprising, in addition to formoterol fumarate (e.g., 10, 15, 20, 25, 30, 35, or 40 mcg of formoterol fumarate (on the equivalent to formoterol free base)), (i) citric acid, (ii) about 5 mg/mL sodium chloride, (iii) water, (iv) about 0.2 or about 0.5 mg/mL edetate disodium, and (v) sodium citrate, where the pH of the composition is from about 5.0 to about 6.0, such as about 5.5. In yet another embodiment is a nebulizable formoterol composition comprising, in addition to formoterol fumarate (e.g., 10, 15, 20, 25, 30, 35, or 40 mcg of formoterol fumarate (on the equivalent to formoterol free base)), (i) about 2 mg/mL citric acid, (ii) about 5 mg/mL sodium chloride, (iii) water, and (iv) about 0.5 mg/mL edetate disodium, where the pH of the composition is from about 5.0 to about 6.0, such as about 5.5.

In certain embodiments, the pH of the nebulizable composition after the tiotropium nebulizable composition is mixed with the formoterol nebulizable composition is from about 4.5 to about 5.5. In certain embodiments, the pH of the nebulizable composition after the tiotropium nebulizable composition is mixed with the formoterol nebulizable composition is about 4.5, about 4.6, about 4.7, about 4.8, about 4.9, about 5.0, about 5.1, about 5.2, about 5.3, about 5.4, or about 5.5.

In one embodiment, the nebulizable formoterol composition is free or substantially free of a preservative (such as a benzalkonium salt, e.g., benzalkonium chloride). In another embodiment, the nebulizable formoterol composition is free or substantially free of a complexing agent, such as ethylene diamine tetra-acetic acid (EDTA) or a salt thereof. For example, the nebulizable formoterol composition may contain less than 0.1% of a complexing agent such as ethylene diamine tetra-acetic acid (EDTA) or a salt thereof, such as less than about 0.05%, less than about 0.02%, less than about 0.01%, or less than about 0.008%, based on total weight of nebulizable formoterol composition. In yet another embodiment, the nebulizable formoterol composition is free or substantially free of both (a) a complexing agent, such as ethylene diamine tetra-acetic acid (EDTA) or a salt thereof, and (b) a preservative, such as a benzalkonium salt, e.g., benzalkonium chloride. For example, the nebulizable formoterol composition may contain less than 0.001% of a complexing agent such as ethylene diamine tetra-acetic acid (EDTA) or a salt thereof and less than 0.001% of a complexing agent, such as ethylene diamine tetra-acetic acid (EDTA) or a salt thereof.

Nebulizable Tiotropium-Formoterol Composition

Another embodiment is a nebulizable tiotropium-formoterol composition comprising a combination of tiotropium or a pharmaceutically acceptable salt thereof and formoterol or a pharmaceutically acceptable salt thereof. The nebulizable tiotropium-formoterol composition is preferably an aqueous solution in which the formoterol or pharmaceutically acceptable salt thereof (preferably formoterol fumarate) and tiotropium or pharmaceutically acceptable salt thereof (preferably tiotropium bromide) are both dissolved (i.e., in solubilized form). The nebulizable tiotropium-formoterol composition may contain tiotropium or a salt thereof (preferably tiotropium bromide) and formoterol or a salt thereof (preferably formoterol fumarate) in the amounts and/or concentrations disclosed above with respect to the nebulizable tiotropium composition and nebulizable formoterol composition, respectively. In one embodiment, the weight ratio of tiotropium bromide and formoterol fumarate in the nebulizable tiotropium-formoterol composition ranges from about 1:256 to about 256:1.

Suitable pharmaceutically acceptable excipients which may be incorporated in the nebulizable formoterol composition include, but are not limited to, isotonicity agents, pH adjusting agents, complexing agents, buffers, surfactants, anti-oxidants, and pharmaceutically acceptable vehicles. The specific excipients and their amounts disclosed above also apply to the nebulizable tiotropium-formoterol composition. The pH of the nebulizable tiotropium-formoterol composition may be from about 1 to about 7, such as from about 4.5 to about 5.5 (for example, about 4.5, about 4.6, about 4.7, about 4.8, about 4.9, about 5.0, about 5.1, about 5.2, about 5.3, about 5.4, or about 5.5).

In one embodiment, the nebulizable tiotropium-formoterol composition is free or substantially free of a preservative (such as a benzalkonium salt, e.g., benzalkonium chloride). In another embodiment, the nebulizable tiotropium-formoterol composition is free or substantially free of a complexing agent, such as ethylene diamine tetra-acetic acid (EDTA) or a salt thereof. For example, the nebulizable tiotropium-formoterol composition may contain less than 0.1% of a complexing agent such as ethylene diamine tetra-acetic acid (EDTA) or a salt thereof, such as less than about 0.05%, less than about 0.02%, less than about 0.01%, or less than about 0.008%, based on total weight of nebulizable tiotropium-formoterol composition. In yet another embodiment, the nebulizable tiotropium-formoterol composition is free or substantially free of both (a) a complexing agent, such as ethylene diamine tetra-acetic acid (EDTA) or a salt thereof, and (b) a preservative, such as a benzalkonium salt, e.g., benzalkonium chloride. For example, the nebulizable tiotropium-formoterol composition may contain less than 0.001% of a complexing agent such as ethylene diamine tetra-acetic acid (EDTA) or a salt thereof and less than 0.001% of a complexing agent, such as ethylene diamine tetra-acetic acid (EDTA) or a salt thereof.

Yet another embodiment is a nebulizable tiotropium-formoterol composition comprising tiotropium bromide, formoterol fumarate, sodium chloride, optionally sodium citrate and citric acid, hydrochloric acid, optionally sodium hydroxide, water and, optionally, edetate disodium.

In one embodiment, first and second solutions are provided, the first solution includes 10 mcg/mL (0.001%) of Tiotropium bromide anhydrous equivalent to Tiotropium; 0.5 mg/mL (0.05%) of edetate disodium; 9 mg/mL (0.9%) sodium chloride; 0.76 mg/mL citric acid anhydrous, water up to 1 mL, where the first solution has a pH of 2.7. The second solution includes 10 mcg/mL (0.001%) of Formoterol fumarate; 0.5 mg/mL (0.05%) of edetate disodium; 5 mg/mL (0.5%) sodium chloride; 2 mg/mL citric acid dihydrate, water up to 1 mL, where the first solution has a pH of 5.5.

The Nebulizable Compositions

The nebulizable compositions described above are preferably sterile unit dosage forms.

The nebulizable composition(s) described herein are storage stable. For example, in one embodiment, the nebulizable composition(s) described herein contain greater than about 80%, 90%, 95%, 98%, or 99% of the initial amount of tiotropium and/or formoterol (or salts thereof) after storage for 1 month, 3 months, 6 months or 1, 2, or 3 years at about 2-8° C. In another embodiment, the nebulizable composition(s) described herein contain greater than about 80%, 90%, 95%, 98%, or 99% of the initial amount of tiotropium and/or formoterol (or salts thereof) after storage for 1 month, 3 months, or 6 months or 1, 2, or 3 years at about 25° C. and 60% relative humidity. In yet another embodiment, the nebulizable composition(s) described herein contain greater than about 80%, 90%, 95%, 98%, or 99% of the initial amount of tiotropium and/or formoterol (or salts thereof) after storage for 1 month, 3 months, or 6 months at about 40° C. and 75% relative humidity.

In one embodiment, any of the aforementioned nebulizable compositions containing tiotropium or a salt thereof and subjected to the storage conditions noted above contain less than about 1%, 0.5%, 0.3%, 0.2%, or 0.1% of tiotropium impurity A (2-hydroxy-2,2-dithiophen-2-ylacetic acid) or tiotropium impurity G ((1R,2R,4S,5S,7s)-7-hydroxy-9,9-dimethyl-3-oxa-9-azoniatricyclo[3.3.1.02,4]nonane bromide) after storage.

| Impurity name | Maximum limit |
|---|---|
| A: 2-hydroxy-2,2-dithiophen-2-ylacetic acid | 1% |
| G: (1R,2R,4S,5S,7s)-7-hydroxy-9,9-dimethyl-3-oxa-9-azoniatricyclo[3.3.1.02,4]nonane bromide | 1% |

In another embodiment, any of the aforementioned nebulizable compositions containing formoterol or a salt thereof and subjected to the storage conditions noted above contain less than about 10%, 7%, 5%, 3%, 2%, 1%, 0.5%, 0.3%, 0.2%, or 0.1% of formoterol impurity A (1-(3-amino-4-hydroxyphenyl)-2-[[2-(4-methoxyphenyl)-1-methylethyl]amino]ethanol) or formoterol impurity G (2RS)-1-(4-methoxyphenyl)-propan-2-amine) after storage.

| Impurity name | Maximum limit |
|---|---|
| A: 1-(3-amino-4-hydroxyphenyl)-2-[[2-(4-methoxyphenyl)-1-methylethyl]amino]ethanol | 10% |
| G: 2RS)-1-(4-methoxyphenyl)-propan-2-amine | 1% |

Containers and Kits

In one embodiment, the tiotropium and formoterol (such as tiotropium bromide and formoterol fumarate) are formulated separately and contained in separate containers or a dual chamber container, which are then mixed prior to or at the time of administration to a patient (e.g., a human patient). For example, a nebulizable tiotropium composition comprising tiotropium bromide and one or more pharmaceutically acceptable excipients can be contained in one chamber and a nebulizable formoterol composition comprising formoterol fumarate and one or more pharmaceutically acceptable excipients contained in a separate chamber. This combination comprising separate compositions of tiotropium bromide and formoterol fumarate can be contained in a dual chamber container. The two chambers of the dual chamber container may be separate or may be connected by a common septum. The dual chamber container with a common septum may contain a common top which when broken would provide simultaneous access to both compositions. The nebulizable tiotropium composition may be mixed with the nebulizable formoterol composition before being added to the reservoir of the nebulizer. In one instance, the nebulizable tiotropium composition may be added to the reservoir of the nebulizer followed by addition of the second nebulizable formoterol composition or vice versa. In this instance, the two compositions would be mixed in the reservoir of the nebulizer device and then administered to the patient.

Yet another embodiment is one or more prefilled containers containing a nebulizable tiotropium composition, a nebulizable formoterol composition, or a combination thereof. Yet another embodiment is one or more prefilled containers containing a nebulizable tiotropium-formoterol composition.

The nebulizable compositions (e.g., both the nebulizable tiotropium composition and the nebulizable formoterol composition) may be in a prepackaged, sterile, premixed, premeasured inhalation solution. Preferably, the solution is a ready-to-use solution which does not require any mixing or dilution by the patient (or subject) prior to administration. The solution may be administered for the relief of bronchospasm in a subject suffering from COPD.

The present invention also relates to a prefilled container containing one or more of the nebulizable compositions of the present invention (for example, containing both the nebulizable tiotropium composition and the nebulizable formoterol composition). In one embodiment, each container comprises a single unit dose of a nebulizable composition of the present invention comprising a therapeutically effective amount of tiotropium or its salt and/or formoterol or its salt for the treatment of COPD. In one embodiment, each container includes a sterile, premixed, premeasured, substantially benzalkonium chloride free inhalation solution comprising a single unit dose of a therapeutically effective amount of tiotropium or its salt and/or formoterol or its salt in a single container.

Yet another embodiment is one or more prefilled containers containing a nebulization composition of the present invention. In one embodiment, each container comprises a single unit dose of a nebulizable composition of the present invention comprising a therapeutically effective amount of tiotropium or its salt or formoterol or its salt for the treatment of COPD. In one embodiment, each container includes a sterile, premixed, premeasured, substantially benzalkonium chloride free inhalation solution comprising a single unit dose of a therapeutically effective amount of tiotropium or its salt or formoterol or its salt in a single container.

One embodiment is a prefilled container containing about 0.5 to 5 mL of an aqueous nebulizable composition comprising (i) from about 1 µg to about 100 µg of tiotropium bromide, (ii) sodium chloride, (iii) hydrochloric acid (e.g., in an amount sufficient to adjust the pH of the pharmaceutical composition, such as to a pH of about 2.5 to about 3.5), and (iv) about 0.01% by weight of disodium EDTA, wherein the composition is free of preservative, and the composition has a pH of from about 2.5 to about 3.5. The sodium chloride may be present at about 0.9% by weight. In one embodiment, the pH of the nebulizable composition is about 2.7. In another embodiment, the pH of the nebulizable composition is about 2.8. In yet another embodiment, the pH of the nebulizable composition is about 2.9. In yet another embodiment, the pH of the nebulizable composition is about 3.0.

Another embodiment is a prefilled container containing about 0.5 to 5 mL of an aqueous nebulizable composition comprising (i) from about 1 µg to about 100 µg of tiotropium bromide, (ii) sodium chloride, (iii) hydrochloric acid (e.g., in an amount sufficient to adjust the pH of the pharmaceutical composition, such as to a pH of about 2.5 to about 3.5), and (iv) about 0.02% by weight of disodium EDTA, wherein the composition is free of preservative, and the composition has a pH of from about 2.5 to about 3.5.

Another embodiment is a prefilled container containing about 0.5 to 5 mL of an aqueous nebulizable composition comprising (i) from about 1 µg to about 100 µg of tiotropium bromide, (ii) sodium chloride, (iii) hydrochloric acid (e.g., in an amount sufficient to adjust the pH of the composition, such as to a pH of about 2.5 to about 3.5), and (iv) about 0.05% by weight of disodium EDTA, wherein the composition is free of preservative, and the composition has a pH of from about 2.5 to about 3.5.

One embodiment is a prefilled container containing about 0.5 to 5 mL of an aqueous pharmaceutical composition comprising (i) from about 1 µg to about 100 µg of formoterol fumarate, (ii) sodium chloride, (iii) citric acid and sodium citrate (e.g., in an amount sufficient to adjust the pH of the composition, such as to a pH of about 5.0 to about 6.0), and (iv) about 0.01% by weight of disodium EDTA, wherein the composition is free of preservative, and the composition has a pH of from about 5.0 to about 6.0. The sodium chloride may be present at about 0.9% by weight. In one embodiment, the pH of the pharmaceutical composition is about 5.5.

Another embodiment is a prefilled container containing about 0.5 to 5 mL of an aqueous nebulizable composition comprising (i) from about 1 µg to about 100 µg of formoterol fumarate, (ii) sodium chloride, (iii) citric acid and sodium citrate (e.g., in an amount sufficient to adjust the pH of the pharmaceutical composition, such as to a pH of about 5.0 to about 6.0), and (iv) about 0.02% by weight of disodium EDTA, wherein the composition is free of preservative, and the composition has a pH of from about 5.0 to about 6.0.

Another embodiment is a prefilled container containing about 0.5 to 5 mL of an aqueous nebulizable composition comprising (i) from about 1 µg to about 100 µg of formoterol fumarate, (ii) sodium chloride, (iii) citric acid and sodium citrate (e.g., in an amount sufficient to adjust the pH of the pharmaceutical composition, such as to a pH of about 5.0 to about 6.0), and (iv) about 0.05% by weight of disodium EDTA, wherein the composition is free of preservative, and the composition has a pH of from about 5.0 to about 6.0.

In one embodiment, the nebulizable compositions described herein comprise a premixed, premeasured aqueous formulation comprising a single unit dose of a therapeutically effective amount of tiotropium or a pharmaceutically acceptable salt thereof and/or formoterol or a pharmaceutically acceptable salt thereof for treating an inflammatory or obstructive airway disease such as asthma and COPD, wherein the amount of tiotropium or its pharmaceutically acceptable salt thereof ranges from about 1 µg to about 100 µg and formoterol or its pharmaceutically acceptable salt in the nebulization composition ranges from about 1 µg to about 100 µg, the nebulizable composition being provided in a prefilled container.

In one embodiment, the nebulizable compositions described herein comprise a sterile, premixed, premeasured aqueous composition substantially free of benzalkonium chloride comprising a single unit dose of a therapeutically effective amount of tiotropium or its pharmaceutically acceptable salt and/or formoterol or its pharmaceutically acceptable salt for treating an inflammatory or obstructive airway disease such as asthma and COPD, wherein the amount of tiotropium or its pharmaceutically acceptable salt thereof or formoterol or its pharmaceutically acceptable salt thereof in the solution ranges from about 1 µg to about 100 µg, the nebulization composition being provided in a single prefilled container and wherein the nebulization composition is suitable for nebulization in a nebulizer.

The present invention also is directed to a kit for treating an inflammatory or obstructive airway disease such as asthma and COPD, the kit comprising: (a) one or more prefilled containers; the one or more prefilled containers each comprising a premixed, premeasured nebulizable composition comprising a single unit dose of a therapeutically effective amount of tiotropium or its pharmaceutically acceptable salt or formoterol or its pharmaceutically acceptable salt thereof; wherein the amount of tiotropium or its pharmaceutically acceptable salt or formoterol or its pharmaceutically acceptable salt in the nebulizable composition ranges from about 1 µg to about 100 µg; the nebulization composition being suitable for nebulization in a nebulizer.

In another embodiment, separate containers or a dual chamber container are respectively prefilled with first solution (Example 4) and the second solution (Example 7), where the first solution includes 10 mcg/mL (0.001%) of Tiotropium bromide anhydrous equivalent to Tiotropium; 0.5 mg/mL (0.05%) of edetate disodium; 9 mg/mL (0.9%) sodium chloride; 0.76 mg/mL citric acid anhydrous, water up to 1 mL, at a pH of 2.7; and the second solution includes 10 mcg/mL (0.001%) of Formoterol fumarate; 0.5 mg/mL (0.05%) of edetate disodium; 5 mg/mL (0.5%) sodium chloride; 2 mg/mL citric acid dihydrate, water up to 1 mL, where the first solution has a pH of 5.5. Alternatively the solutions of Examples 4 and 7 can be combined into a single container, vial, or vessel.

The present invention also is directed to a kit for treating an inflammatory or obstructive airway disease such as asthma and COPD, the kit comprising:
(a) one or more prefilled containers; said one or more prefilled containers each comprising a sterile, premixed, premeasured nebulizable composition substantially free of benzalkonium chloride for use in a nebulizer; the nebulizable composition comprising a single unit dose of a therapeutically effective amount of tiotropium or its pharmaceutically acceptable salt or formoterol or its pharmaceutically acceptable salt, wherein the amount of each of tiotropium and formoterol ranges from about 1 µg to about 100 µg;
(b) a label which indicates that the nebulizable composition can be used for treating an inflammatory or obstructive airway disease such as asthma and COPD; and
(c) instructions for using the nebulizable composition for treating an inflammatory or obstructive airway disease such as asthma and COPD.

Methods of Treatment

In another aspect, the present invention relates to a method for treating an inflammatory or obstructive airway disease such as asthma and COPD, the method comprising:
(a) providing the subject or prescriber a prepackaged therapeutic system comprising: one or more prefilled containers; the one or more prefilled containers containing about 0.5 to 5 ml of a sterile, stable, substantially benzalkonium chloride-free, premixed, premeasured nebulizable composition consisting essentially of a unit dose of a therapeutically effective amount of tiotropium or its pharmaceutically acceptable salt or formoterol or its pharmaceutically acceptable salt; wherein the dose of tiotropium or its pharmaceutically acceptable salt or formoterol or its pharmaceutically acceptable salt is about 1 µg or about 100 µg; the nebulizable composition in each of the one or more prefilled containers is suitable for nebulization in a nebulizer; and
(b) providing the subject or prescriber of the prepackaged therapeutic system indication, adverse reaction, dosage and administration data pertaining to the nebulizable composition in each of the one or more prefilled containers;
wherein the indication data informs the subject or prescriber that the nebulizable composition in each of the one or more prefilled containers is indicated for treating an inflammatory or obstructive airway disease such as asthma and COPD.

In another aspect, the present invention relates to a method of treating an inflammatory or obstructive airway disease such as asthma and COPD in a subject, the method comprising:
(a) administrating to the subject at least one prefilled containers; the one or more prefilled containers each prefilled with about 0.5 ml to about 5 ml of a premixed, premeasured nebulizable composition comprising a unit dose of a therapeutically effective amount of tiotropium or its pharmaceutically acceptable salt or formoterol or its pharmaceutically acceptable salt; wherein the amount of tiotropium or its pharmaceutically acceptable salt or formoterol or its pharmaceutically acceptable salt is each about 1 µg to about 100 µg; the nebulizable composition in each of the one or more prefilled containers is suitable for nebulization in a nebulizer.

In another aspect, the present invention relates to a kit comprising:
(a) a nebulizable composition, comprising tiotropium or its pharmaceutically acceptable salt or formoterol or its pharmaceutically acceptable salt thereof in a pharmacologically suitable fluid, wherein the composition is stable during long term storage, the fluid comprises water, and the composition is formulated at a concentration suitable for direct administration to a subject in need thereof; and
(b) a nebulizer.

Preparation

The nebulizable compositions described herein can be prepared as described in the following non-limiting examples.

A. Composition Comprising Tiotropium and Formoterol Together
  (i) Transfer water for injection previously purged with nitrogen;
  (ii) Add and dissolve pharmaceutically acceptable excipients such as isotonicity adjustors;
  (iii) Adjust the pH to around 1 to 7 by adding buffers;
  (iv) Add and dissolve formoterol fumarate to solution of step (iii);
  (v) Add and dissolve tiotropium bromide to solution of step (iv);
  (vi) Adjust the pH of the solution (v) to 1-7;

(vii) Make up volume with water;
(viii) Filter the solution of step (vii) under aseptic conditions;
(ix) Fill the solution of step (viii) into an low density polyethylene (LDPE) container; and
(x) Pack the LDPE containers into an aluminum pouch and seal.

B. Composition Comprising Tiotropium and Formoterol in Separate Containers

B.1. Composition of Tiotropium
(i) Transfer water for injection previously purged with nitrogen;
(ii) Add and dissolve pharmaceutically acceptable excipients such as isotonicity adjustors;
(iii) Adjust the pH to around 1 to 7 by adding buffers;
(iv) Add and dissolve tiotropium bromide to the solution of step (iii);
(v) Adjust the pH of the solution (iv) to 1-7;
(vi) Make up volume with water;
(vii) Filter the solution of step (vi) under aseptic conditions; and
(viii) Fill the solution of step (vii) into a chamber of the dual chambered LDPE container.

B.2. Composition of Formoterol
(i) Transfer water for injection previously purged with nitrogen;
(ii) Add and dissolve pharmaceutically acceptable excipients such as isotonicity adjustors;
(iii) Adjust the pH to around 1 to 7 by adding buffers;
(iv) Add and dissolve formoterol fumarate to solution of step (iii);
(v) Adjust the pH of the solution (v) to 1-7;
(vi) Make up volume with water;
(vii) Filter the solution of step (vi) under aseptic conditions;
(viii) Fill the solution of step (vi) into another chamber of the dual chambered LDPE container; and
(ix) Pack the LDPE containers into an aluminium pouch and seal.

B.3 Mixing Compositions B.1 and B.2
(i) Mix the nebulization compositions B.1 and B.2 to obtain a nebulization composition B.3; and
(ii) Add the B.3 nebulization composition to the reservoir of the nebulizer device; or
(iii) Nebulization compositions B.1 and B.2 can be separately added to the reservoir of the nebulizer device and mixed to form a nebulization composition B.3

In another embodiment, a formulation for nebulization including the nebulizable compositions disclosed herein is prepared for nebulization by emptying tiotropium and formoterol compositions described herein, from either a single chamber or dual chamber container together or sequentially into a reservoir of a nebulizer device, mixing the tiotropium and formoterol compositions to obtain a nebulizable composition, and operating the device to nebulize the nebulizable composition.

A nebulizable composition of the present invention may have a fill volume of from about 0.5 ml to about 5 ml. The nebulizable composition may be present in a prefilled container, wherein the volume of the composition is from about 0.1 ml to about 5 ml, such as from about 0.2 ml to about 4 ml, such as from about 1 ml to about 3 ml, or from about 1.5 ml to about 2.5 ml. In another embodiment, the volume of the nebulizable composition of the present invention is from about 0.05 ml to about 1.0 ml; such as from about 0.1 ml to about 0.9 ml; from about 0.1 ml to about 0.8 ml; from about 0.1 ml to about 0.7 ml; from about 0.1 ml to about 0.6 ml; from about 0.1 ml to about 0.5 ml; from about 0.1 ml to about 0.4 ml; from about 0.1 ml to about 0.3 ml; or from about 0.1 ml to about 0.2 ml.

The nebulizable compositions provided herein has a long shelf life, i.e., it is stable during long term storage. For example, the nebulizable compositions described herein may contain greater than about 80%, such as greater than about 85%, greater than about 90%, greater than about 95% or greater than about 98% of the initial amount of tiotropium (or its salt) and formoterol (or its salt) in the composition after being stored for about 3 or 6 months or about 1, 2 or 3 years at 2-8° C. and 25° C. when stored in a suitable container (such as a LDPE container in an aluminum pouch). The stability may be determined using Arrhenius kinetics.

The nebulizable composition may be contained in a unit-dose, low-density polyethylene (LDPE) container. Each unit-dose container may be disposed in a foil pouch, and each foil pouch may contain one or more unit-dose containers. Each foil pouch containing the unit dose container may be disposed in a shelf carton. The container may have a TWIST-FLEX™ top, such top comprising an easy-to-grip tab-like handle such that the container may be opened, for example, by twisting off the tab by hand. The TWIST-FLEX™ top is advantageous in that it allows for easy dispensing of the solution, prevents spillage and eliminates the need to open the container by cutting or tearing off the top, thereby reducing cross-contamination. One or more of the single unit dose containers may be prepackaged in an aluminum foil pouch, such that the foil provides a protective barrier against environmental contaminants and light as it helps to improve the shelf-life and stability of the nebulization composition. Dispensing vials may include, but are not limited to, any container comprising glass, low density polyethylene, or any other material capable of preventing the solution from leaking out of the container. The vial may be enclosed by any conventional means including, but not limited to, screw cap, heat seal, snap-on top, flip-top, twist-off stopper, and peel away top.

The nebulizable composition(s) may be administered by nebulizer. Suitable nebulizers include, but are not limited to, a jet nebulizer, an ultrasonic nebulizer, vibrating mesh nebulizer and a breath actuated nebulizer. The nebulizable composition(s) may be administered by nebulizers manufactured, designed or sold by Omron, such as the Omron MICRO AIR™ Ultrasonic Nebulizer or those manufactured, designed, or sold by Aerogen, or with the Nebu-Tec device, M-Neb® or with the Zephair® device from Aerosonix, or with the Fox Inhaler® from Vectura, or with the Alphazer® device from Omega or with the Micro® device, Innospire Go device and i-Neb advance device from Philips Additionally, the nebulizable compositions described herein can also be nebulized using inhalers other than those described above.

The nebulizable compositions also may be provided as a kit wherein the kit comprises a nebulizer and the nebulizable composition comprising tiotropium bromide and formoterol fumarate.

Yet another embodiment is a method of relieving bronchospasm (such as that associated with COPD) comprising administering by inhalation to a subject in need thereof one or more nebulizable compositions according to any of the embodiments described herein.

Yet another embodiment is a kit and/or system for administering a bronchodilator to relieve bronchospasm, for instance, bronchospasm associated with COPD. The kit and/or system may comprise a nebulizable composition according to any of the embodiments described herein. In one embodiment, the kit and/or system comprises a nebulization composition of the present invention in a prepackaged, premeasured, premixed and/or single unit dose form for the treatment of COPD. In another embodiment, the prepackaged inhalation kit and/or system comprises one or more premixed, premeasured single unit dose vials comprising a nebulizable composition of the present invention for the treatment of bronchospasm (such as that associated with COPD), and instructions for using the same.

Yet another embodiment is a kit comprising a nebulizer, instructions for using the nebulizer and the unit dose vials containing the nebulizable compositions according to any of the embodiments described herein.

Yet another embodiment is a kit for the treatment, prevention or amelioration or one or more symptoms of diseases or disorders associated with bronchoconstriction, the kit comprising:

(i) a nebulizer;
(ii) a nebulizable composition for the treatment, prevention or amelioration or one or more symptoms of diseases or disorders associated with bronchoconstriction, the composition comprising:
(a) tiotropium or a pharmaceutically acceptable salt thereof;
(b) formoterol or a pharmaceutically acceptable salt thereof; and
(c) water.
and wherein the nebulizable composition is substantially free of preservative.

Another embodiment of the invention relates to a device comprising tiotropium or a pharmaceutically acceptable salt thereof and formoterol or a pharmaceutically acceptable salt thereof, for example, for use in relieving the symptoms of COPD.

Yet another embodiment is a method for improving user compliance and/or quality of life as compared to conventional treatments for COPD. The method comprises initiating treatment with a pharmaceutical composition or solution according to any of the embodiments described herein, or a container, kit, or system or a pharmaceutically acceptable salt thereof. The present invention provides convenient, fast and reliable treatment for COPD that represents an improvement over traditional COPD treatments.

The present invention also includes methods of treating an inflammatory or obstructive airway disease such as asthma and COPD by administering to a patient a nebulizable composition comprising tiotropium (or its salt) and formoterol (or its salt) according to any of the embodiments described herein via a nebulizer.

Throughout this specification it is to be understood that the words "comprise" and "include" and variations such as "comprises", "comprising", "includes", "including" are to be interpreted inclusively, unless the context requires otherwise. That is, the use of these words may imply the inclusion of an element or elements not specifically recited.

EXAMPLES

The following examples further illustrate the invention, but are not limiting.

Nebulizable Compositions Comprising Tiotropium Bromide and Formoterol Fumarate in a Single Composition The following examples illustrate nebulization compositions comprising tiotropium and formoterol together in a single composition.

| # | Ingredient | #1 (mg/mL) | #2 (mg/mL) | #3 (mg/mL) | #4 (mg/mL) | #5 (mg/mL) |
|---|---|---|---|---|---|---|
| 1 | Tiotropium bromide equivalent to tiotropium base | 0.00125-0.64 | 0.00125-0.64 | 0.00125-0.64 | 0.00125-0.64 | 0.00125-0.64 |
| 2 | Formoterol fumarate dihydrate equivalent to formoterol fumarate | 0.0025-0.32 | 0.0025-0.32 | 0.0025-0.32 | 0.0025-0.32 | 0.0025-0.32 |
| 3 | Sodium chloride | 9 | 9 | 9 | 9 | 9 |
| 4 | Sodium citrate (as 10% solution) | q.s. to pH | — | — | — | — |
| 5 | Citric acid (as 10% solution) | q.s. to pH | — | — | — | — |
| 6 | Edetate disodium | — | 0.010 | — | 0.010 | — |
| 7 | Hydrochloric acid | — | q.s. to pH | q.s. to pH | q.s. to pH | q.s. to pH |
| 8 | Sodium hydroxide | — | q.s. to pH | q.s. to pH | — | — |
| 9 | Water for injection | q.s. to 1 mL | q.s. to 1 mL | q.s. to 1 mL | q.s. to 1 mL | q.s. to 1 mL |

Manufacturing Process
1. Collect 120% of water for injection of a total batch size in a stainless steel (SS) vessel. Purge with nitrogen or without nitrogen;
2. From the above step, transfer 90% of the water for injection of a total batch size in another SS vessel.
3. To step 2 add and dissolve a batch quantity of sodium chloride/edetate disodium.
4. Adjust the pH to between 1 to 7.
5. To step 4, add and dissolve a batch quantity of formoterol fumarate dihydrate.
6. To step 5, add and dissolve a batch quantity of tiotropium bromide.
7. Check and adjust the pH of the above bulk solution to between 1.0 and 7.0 with sodium citrate (as 10% solution) and/or citric acid (as 10% solution) OR hydrochloric acid and/or sodium hydroxide.
8. Make up the volume to 100% of the above bulk solution with water for injection
9. Filter the solution aseptically.
10. Fill in LDPE container (Fill volume: 0.5 mL to 5 mL) and packed in aluminium pouch and seal.

Examples of Nebulizable Composition Comprising Tiotropium Bromide and Formoterol Fumarate Prepared Separately and to be Mixed Prior to Administration The following examples illustrate compositions of tiotropium and formoterol which are formulated separately and are mixed prior to administration to a patient.

B.1 Nebulization Compositions Comprising Tiotropium Bromide

Example 1

| # | Ingredient | # 1 (mg/mL) | # 2 (mg/mL) | # 3 (mg/mL) | # 4 (mg/mL) | # 5 (mg/mL) |
|---|---|---|---|---|---|---|
| 1 | Tiotropium bromide equivalent to tiotropium base | 0.00125-0.64 | 0.00125-0.64 | 0.00125-0.64 | 0.00125-0.64 | 0.00125-0.64 |
| 2 | Sodium chloride | 9 | 9 | 9 | 9 | 9 |
| 3 | Sodium citrate (as 10% solution) | q.s. to pH | — | — | — | — |
| 4 | Citric acid (as 10% solution) | q.s. to pH | — | — | — | — |
| 5 | Edetate disodium | — | 0.010 | — | 0.010 | — |
| 6 | Hydrochloric acid | — | q.s. to pH | q.s. to pH | q.s. to pH | q.s. to pH |
| 7 | Sodium hydroxide | — | q.s. to pH | q.s. to pH | — | — |
| 8 | Water for injection | q.s. to 1 mL | q.s. to 1 mL | q.s. to 1 mL | q.s. to 1 mL | q.s. to 1 mL |

Manufacturing Process
1. Collect 120% of water for injection of a total batch size in stainless steel (SS) vessel. Purge with nitrogen.
2. From the above step, transfer 90% of the water for injection of a total batch size in another stainless steel (SS) vessel.
3. To step 2 add and dissolve a batch quantity of sodium chloride/edetate disodium.
4. Adjust the pH to between 1 to 7.
5. To step 4, add and dissolve a batch quantity of tiotropium bromide.
6. Check and adjust the pH of the above bulk solution to between 1.0 and 7.0 with sodium citrate (as 10% solution) and/or citric acid (as 10% solution) OR hydrochloric acid and/or sodium hydroxide.
7. Make up the volume to 100% of the above bulk solution with water for injection.
8. Filter the solution aseptically.
9. Fill in LDPE container (Fill volume: 0.5 mL to 5 mL) and packed in aluminium pouch and seal.

Example 2

| Sr. No | Ingredients | Unit Quantity |
|---|---|---|
| 1 | Tiotropium bromide anhydrous equivalent to Tiotropium | 10 mcg/mL (0.001%) |
| 2 | Edetate disodium | 0.2 mg/mL (0.02%) |
| 3 | Sodium chloride | 9 mg/mL (0.9%) |
| 4 | Citric acid anhydrous | 2 mg/mL (0.2%) |
| 5 | Water for injection | q.s. to 1 mL |
| 6 | pH | 2.7 |

Stability Data:

| | | | | Related substances (%) | | | | | | |
|---|---|---|---|---|---|---|---|---|---|---|
| Condition | pH | Osm (mOsm/Kg) | Assay (%) | Imp ED TG | Imp. A | Imp. B | Imp. E | Imp. F | Single Maximum Unknown impurity | Total Impurities |
| INITIAL | 2.66 | 299 | 100.15 | 0 | 0.05 | 0 | 0 | 0 | 0.05 | 0.1 |
| 1 M/2-8° C. | 2.64 | 294 | 99.6 | 0 | 0 | 0.05 | 0 | 0 | 0.06 | 0.11 |
| 2 M/2-8° C. | 2.68 | 288 | 103.75 | 0 | 0 | 0.05 | 0 | 0 | 0.05 | 10 |
| 3 M/2-8° C. | 2.53 | 299 | 106.1 | 0 | 0.03 | 0 | 0 | 0 | BDL | BDL |
| 6 M/2-8° C. | 2.66 | 291 | 110.25 | 0 | 0.02 | 0 | 0 | 0 | ND | 0.02 |
| 1 M/25° C./60% RH | 2.63 | 292 | 99.3 | 0 | BDL | 0 | 0 | 0 | BDL | BDL |
| 2 M/25° C./60% RH | 2.59 | 289 | 103.35 | 0 | 0.05 | 0.06 | 0 | 0 | 0.05 | 0.16 |
| 3 M/25° C./60% RH | 2.52 | 300 | 105.85 | 0 | 0.12 | 0 | 0 | 0 | BDL | 0.12 |
| 6 M/25° C./60% RH | 2.64 | 287 | 112.05 | 0 | 0.15 | 0 | 0 | 0 | ND | 0.15 |
| 1 M/40° C./75% RH | 2.62 | 295 | 99.1 | 0 | 0.15 | 0 | 0 | 0 | 0.07 | 0.22 |
| 2 M/40° C./75% RH | 2.58 | 287 | 103.85 | 0 | 0.23 | 0.07 | 0 | 0 | 0 | 0.35 |
| 3 M/40° C./75% RH | 2.52 | 299 | 104.6 | 0 | 0.4 | 0 | 0 | 0 | 0.19 | 0.7 |
| 6 M/40° C./75% RH | 2.65 | 292 | 111.9 | 0 | 0.49 | 0 | 0 | 0 | 0.04 | 0.48 |

Impurity A: 2-hydroxy-2,2-dithiophen-2-ylacetic acid (max. limit 1%)

Impurity G: : (1R,2R,4S,5S,7s)-7-hydroxy-9,9-dimethyl-3-oxa-9-azoniatricyclo[3.3.1.02,4]nonane bromide (max. limit 1%)

Example 3

| Sr. No | Ingredients | Unit quantity |
|---|---|---|
| 1 | Tiotropium bromide anhydrous equivalent to Tiotropium | 10 mcg/mL (0.001%) |
| 2 | Edetate disodium | 0.5 mg/mL (0.05%) |
| 3 | Sodium chloride | 9 mg/mL (0.9%) |
| 4 | Citric acid anhydrous | 2 mg/mL (0.2%) |
| 5 | Water for injection | q.s. to 1 mL |
| 6 | pH | 2.7 |

Stability Data:

| Condition | pH | Osm (mOsm/Kg) | Assay (%) | Imp ED TG | Imp A | Imp B | Imp E | Imp F | Single Maximum Unknown impurity | Total Impurities |
|---|---|---|---|---|---|---|---|---|---|---|
| INITIAL | 2.5 | 300 | 100.9 | 0 | 0 | 0 | 0 | 0 | 0.05 | 0.05 |
| 1 M/2-8° C. | 2.41 | 307 | 104.35 | 0 | 0.06 | 0 | 0 | 0 | 0.09 | 0.2 |
| 2 M/2-8° C. | 2.43 | 300 | 105.35 | 0 | 0 | 0 | 0 | 0 | 0.09 | 0.09 |
| 3 M/2-8° C. | 2.43 | 303 | 104 | 0 | 0.07 | 0 | 0 | 0 | 0.06 | 0.18 |
| 6 M/2-8° C. | 2.47 | 298 | 107.2 | 0 | 0.02 | 0 | 0 | 0 | 0.12 | 0.21 |
| 1 M/25° C./60% RH | 2.43 | 305 | 104.2 | 0 | 0 | 0 | 0 | 0 | 0.07 | 0.07 |
| 2 M/25° C./60% RH | 2.42 | 301 | 105.75 | 0 | 0 | 0 | 0 | 0 | 0.07 | 0.07 |
| 3 M/25° C./60% RH | 2.41 | 305 | 104 | 0 | 0.11 | 0 | 0 | 0 | 0.06 | 0.27 |
| 6 M/25° C./60% RH | 2.39 | 297 | 108.7 | 0 | 0.18 | 0 | 0 | 0 | 0 | 0.18 |
| 1 M/40° C./75% RH | 2.44 | 308 | 104.25 | 0 | 0.12 | 0 | 0 | 0 | 0.05 | 0.22 |
| 2 M/40° C./75% RH | 2.42 | 303 | 102.15 | 0 | 0.26 | 0 | 0 | 0 | 0 | 0.26 |
| 3 M/40° C./75% RH | 2.41 | 301 | 103.35 | 0 | 0.35 | 0 | 0 | 0 | 0.06 | 0.54 |
| 6 M/40° C./75% RH | 2.38 | 299 | 107.6 | 0 | 0.51 | 0 | 0 | 0 | 0.12 | 0.7 |

Example 4

| Sr. No | Ingredients | Unit quantity |
|---|---|---|
| 1 | Tiotropium bromide anhydrous equivalent to Tiotropium | 10 mcg/mL (0.001%) |
| 2 | Edetate disodium | 0.5 mg/mL (0.05%) |
| 3 | Sodium chloride | 9 mg/mL (0.9%) |
| 4 | Citric acid anhydrous | 0.76 mg/mL (pH2.7) |
| 5 | Water for injection | q.s. to 1 mL |
| 6 | pH | 2.7 |

Stability Data:

| Condition | pH | Osm (mOsm/Kg) | Assay (%) | Imp ED TG | Imp A | Imp B | Imp E | Imp F | Single Maximum Unknown impurity | Total Impurities |
|---|---|---|---|---|---|---|---|---|---|---|
| INITIAL | 2.82 | 292 | 99.85 | 0 | 0 | 0 | 0 | 0 | 0.05 | 0.1 |
| 1 M/2-8° C. | 2.8 | 298 | 103.7 | 0 | ND | 0 | 0 | 0 | BDL | BDL |
| 3 M/2-8° C. | 2.66 | 292 | 100.35 | 0 | 0.08 | 0 | 0 | 0 | 0.05 | 0.22 |
| 6 M/2-8° C. | 2.78 | 292 | 104.8 | 0 | 0.04 | 0 | 0 | 0 | 0 | 0.04 |
| 1 M/25° C./40% RH | 2.8 | 298 | 103.6 | 0 | 0.07 | 0 | 0 | 0 | 0.04 | 0.07 |

-continued

| Condition | pH | Osm (mOsm/Kg) | Assay (%) | Related substances (%) Imp ED TG | Imp A | Imp B | Imp E | Imp F | Single Maximum Unknown impurity | Total Impurities |
|---|---|---|---|---|---|---|---|---|---|---|
| 3 M/25° C./ 40% RH | 2.65 | 294 | 99.85 | 0 | 0.18 | 0 | 0 | 0 | 0 | 0.18 |
| 6 M/25° C./ 40% RH | 2.79 | 288 | 105.15 | 0 | 0.3 | 0 | 0 | 0 | 0 | 0.3 |
| 1 M/40° C./ 25% RH | 2.81 | 300 | 103.65 | 0 | 0.18 | 0 | 0 | 0 | 0.04 | 0.18 |
| 3 M/40° C./ 25% RH | 2.66 | 300 | 100.5 | 0 | 0.5 | 0 | 0 | 0 | 0.04 | 0.54 |
| 6 M/40° C./ 25% RH | 2.79 | 301 | 107.2 | 0 | 0.82 | 0 | 0 | 0 | 0 | 0.82 |

B.2 Nebulizable Compositions Comprising Formoterol Fumarate

Example 5

| # | Ingredient | # 1 (mg/mL) | # 2 (mg/mL) | # 3 (mg/mL) | # 4 (mg/mL) | # 5 (mg/mL) |
|---|---|---|---|---|---|---|
| 1 | Formoterol fumarate dehydrate equivalent to formoterol fumarate | 0.0025-0.32 | 0.0025-0.32 | 0.0025-0.32 | 0.0025-0.32 | 0.0025-0.32 |
| 2 | Sodium chloride | 9 | 9 | 9 | 9 | 9 |
| 3 | Sodium citrate (as 10% solution) | q.s. to pH | — | — | — | — |
| 4 | Citric acid(as 10% solution) | q.s. to pH | — | — | — | — |
| 5 | Edetate disodium | — | 0.010 | — | 0.010 | — |
| 6 | Hydrochloric acid | — | q.s. to pH | q.s. to pH | q.s. to pH | q.s. to pH |
| 7 | Sodium hydroxide | — | q.s. to pH | q.s. to pH | — | — |
| 8 | Water for injection | q.s. to 1 mL | q.s. to 1 mL | q.s. to 1 mL | q.s. to 1 mL | q.s. to 1 mL |

Manufacturing Process

1. Collect 120% of water for injection of a total batch size in stainless steel (SS) vessel. Purge with nitrogen.
2. From the above step, transfer 90% of water for injection of total batch size in another stainless steel (SS) vessel.
3. To step 2 add and dissolve a batch quantity of sodium chloride/edetate disodium.
4. Adjust the pH to between 1 to 7
5. To step 4, add and dissolve a batch quantity of formoterol fumarate dihydrate.
6. Check and adjust the pH of the above bulk solution between 1.0 and 7.0 with sodium citrate (as 10% solution) and/or citric acid (as 10% solution) OR hydrochloric acid/sodium hydroxide.
7. Make up the volume to 100% of the above bulk solution with water for injection
8. Filter the solution aseptically
9. Fill in LDPE container (Fill volume: 0.5 mL to 5 mL) and packed in aluminium pouch and seal.

Example 6

| Sr. No | Ingredients | Unit Quantity |
|---|---|---|
| 1 | Formoterol fumarate | 10 mcg/mL (0.001%) |
| 2 | Edetate disodium | 0.2 mg/mL (0.02%) |
| 3 | Sodium chloride | 5 mg/mL (0.5%) |
| 4 | Citric acid anhydrous | 2 mg/mL (0.2%) |
| 5 | Sodium citrate dihydrate | 13.2 mg/mL (1.32%) |
| 6 | Water for injection | q.s. to 1 mL |
| 7 | pH | 5.5 |

Stability Data:

| Condition | pH | Osmolality (mOsm/Kg) | Assay (%) | Related substances (%) Imp G | Imp A | Imp B | Imp C | Imp D | Imp E | Imp F | Imp H | Single Maximum Unknown impurity | Total Impurities |
|---|---|---|---|---|---|---|---|---|---|---|---|---|---|
| INITIAL | 5.46 | 297 | 103.4 | 0.0 | 0.09 | 0.0 | 0.0 | 0.0 | 0.0 | 0.0 | 0.0 | ND | 0.09 |
| 1 M-2°-8° C. | 5.42 | 302 | 105.95 | 0.0 | 0.25 | 0.0 | 0.0 | 0.0 | 0.0 | 0.0 | 0.0 | ND | 0.25 |
| 2 M-2°-8° C. | 5.36 | 302 | 106.15 | 0.0 | 0.29 | 0.0 | 0.0 | 0.0 | 0.0 | 0.0 | 0.0 | ND | 0.29 |
| 3 M-2°-8° C. | 5.32 | 311 | 105.1 | 0.0 | 0.38 | 0.0 | 0.0 | 0.0 | 0.0 | 0.0 | 0.0 | ND | 0.38 |
| 6 M-2°-8° C. | 5.43 | 306 | 103.8 | 0.0 | 0.62 | 0.0 | 0.0 | 0.0 | 0.0 | 0.0 | 0.0 | ND | 0.62 |

-continued

|  |  |  |  | Related substances (%) |  |  |  |  |  |  |  |  |  |
|---|---|---|---|---|---|---|---|---|---|---|---|---|---|---|
| Condition | pH | Osmolality (mOsm/Kg) | Assay (%) | Imp G | Imp A | Imp B | Imp C | Imp D | Imp E | Imp F | Imp H | Single Maximum Unknown impurity | Total Impurities |
| 1 M-25° C./60% RH | 5.42 | 306 | 104.9 | 0.0 | 1.15 | 0.0 | 0.0 | 0.0 | 0.0 | 0.0 | 0.0 | 0.39 (0.73) | 1.58 |
| 3 M-25° C./60% RH |  | Not Done |  | 0.0 | 2.76 | 0.0 | 0.0 | 0.0 | 0.0 | 0.0 | 0.0 | 0.74 (0.75) | 3.97 |
| 6 M-25° C./60% RH | 5.33 | 308 | 98.45 | 0.1 | 4.57 | 0.0 | 0.0 | 0.0 | 0.0 | 0.0 | 0.0 | 0.29 (0.24) | 5.15 |
| 1 M-40° C./75% RH | 5.42 | 304 | 98.8 | 0.0 | 4.83 | 0.0 | 0.0 | 0.0 | 0.0 | 0.0 | 0.0 | 0.43 (0.53) | 5.44 |

Example 7

| Sr. No | Ingredients | Unit Quantity |
|---|---|---|
| 1 | Formoterol fumarate | 10 mcg/mL (0.001%) |
| 2 | Edetate disodium | 0.5 mg/mL (0.05%) |
| 3 | Sodium chloride | 5 mg/mL (0.5%) |
| 4 | Citric acid anhydrous | 2 mg/mL (0.2%) |
| 5 | Sodium citrate dihydrate | 13.2 mg/mL (1.32%) |
| 6 | Water for injection | q.s. to 1 mL |
| 7 | pH | 5.5 |

Stability Data:

|  |  |  |  | Related substances (%) |  |  |  |  |  |  |  |  |  |
|---|---|---|---|---|---|---|---|---|---|---|---|---|---|---|
| Condition | pH | Osmolality (mOsm/Kg) | Assay (%) | Imp G | Imp A | Imp B | Imp C | Imp D | Imp E | Imp F | Imp H | Single Maximum Unknown impurity | Total Impurities |
| INITIAL | 5.38 | 306 | 96.5 | 0.0 | 0.3 | 0.0 | 0.0 | 0.0 | 0.0 | 0.0 | 0.0 | ND | 0.3 |
| 1 M-2°-8° C. | 5.48 | 305 | 99.0 | 0.0 | 0.31 | 0.0 | 0.0 | 0.0 | 0.0 | 0.0 | 0.0 | BDL | 0.31 |
| 2 M-2°-8° C. | 5.27 | 333 | 97.7 | 0.0 | 0.38 | 0.0 | 0.0 | 0.0 | 0.0 | 0.0 | 0.0 | BDL | 0.38 |
| 3 M-2°-8° C. | 5.37 | 314 | 103.1 | 0.0 | 0.43 | 0.0 | 0.0 | 0.0 | 0.0 | 0.0 | 0.0 | 0 | 0.43 |
| 6 M-2°-8° C. | 5.39 | 296 | 99.7 | 0.0 | 0.68 | 0.0 | 0.0 | 0.0 | 0.0 | 0.0 | 0.0 | 0.06 | 0.74 |
| 1 M-25° C./60% RH | 5.48 | 305 | 98.55 | 0.0 | 1.06 | 0.0 | 0.0 | 0.0 | 0.0 | 0.0 | 0.0 | 0 | 1.06 |
| 3 M-25° C./60% RH | 5.38 | 310 | 100.35 | 0.0 | 2.17 | 0.0 | 0.0 | 0.0 | 0.0 | 0.0 | 0.0 | 0.33 | 2.5 |
| 6 M-25° C./60% RH | 5.38 | 297 | 94.6 | 0.08 | 3.94 | 0.0 | 0.0 | 0.0 | 0.0 | 0.0 | 0.0 | 0.80 | 4.95 |
| 1 M-40° C./75% RH | 5.48 | 303 | 93.6 | 0.1 | 2.88 | 0.0 | 0.0 | 0.0 | 0.0 | 0.0 | 0.0 | 2.53 | 9.08 |

Impurity A: 1-(3-amino-4-hydroxyphenyl)-2-[[2-(4-methoxyphenyl)-1-methylethyl]amino]ethanol (max. limit 10%)
Impurity G: (2RS)-1-(4-methoxyphenyl)-propan-2-amine (max. limit 1%)

What is claimed is:

1. A dual chamber container suitable for use with a nebulizer and prefilled with a nebulizable composition, comprising in one chamber a first solution of tiotropium or a pharmaceutically acceptable salt thereof and in a second chamber a second solution of formoterol or a pharmaceutically acceptable salt thereof, wherein the first and/or second solution further comprises from about 0.1 to about 1 mg/mL of edetate disodium.

2. The dual chamber container of claim 1, wherein the first solution comprises (a) from about 0.00125 to about 0.64 mg/mL of tiotropium bromide (equivalent to tiotropium base), (b) about 9 mg/mL sodium chloride, (c) optionally edetate disodium, (d) optionally hydrochloric acid, and (e) optionally sodium hydroxide, wherein the pH of the first solution is from about 2 to about 6, and the second solution comprises (a) from about 0.0025 to about 0.32 mg/mL formoterol fumarate dihydrate (equivalent to formoterol fumarate), (b) about 2 to about 10 mg/mL sodium chloride, (c) optionally edetate disodium, (d) optionally hydrochloric acid, and (e) optionally sodium hydroxide, wherein the pH of the second solution is from about 4.5 to about 6.5.

3. The dual chamber container of claim 1, wherein said nebulizable composition is substantially free of preservative.

4. The dual chamber container of claim 1, wherein the two chambers of the dual chamber container may be separate or may be connected by a common septum.

5. The dual chamber container of claim 4, with a common septum and a common top which when broken would provide simultaneous access to the first and second solutions.

6. The dual chamber container of claim 1, further comprising sodium chloride in each chamber.

7. The dual chamber container of claim 1, wherein the second solution comprises formoterol fumarate.

8. The dual chamber container of claim 7, wherein the second solution comprises from about 0.0025 to about 0.32 mg/mL of formoterol fumarate dihydrate.

9. The dual chamber container of claim 1, wherein the first and/or second solution further comprises from about 2 to about 10 mg/mL of sodium chloride.

10. The dual chamber container of claim 1, wherein the first and/or second solution further comprises sodium citrate, citric acid, or any combination thereof.

11. The dual chamber container of claim 1, wherein the first and/or second solution further comprises at least one of hydrochloric acid and sodium hydroxide.

12. The dual chamber container of claim 1, wherein the volume of the composition is about 0.5 to about 5 mL.

13. The dual chamber container of claim 1, wherein said composition is substantially free of preservative.

14. A method of administering tiotropium and formoterol to a patient in need thereof comprising administering to the patient by inhalation with a nebulizer a first solution of tiotropium or a pharmaceutically acceptable salt thereof and a second solution of formoterol or a pharmaceutically acceptable salt thereof, wherein the first solution has a pH of from about 2 to about 6, and the second solution has a pH of from about 4.5 to about 6.5.

15. The method of claim 14, wherein the solutions are combined prior to inhalation.

16. The method of claim 14, wherein the first solution comprises tiotropium bromide.

17. The method of claim 14, wherein the first solution comprises from about 0.00125 to about 0.64 mg/mL of tiotropium bromide (equivalent to tiotropium base).

18. The method of claim 14, wherein the second solution comprises formoterol fumarate.

19. The method of claim 14, wherein the second solution comprises from about 0.0025 to about 0.32 mg/mL of formoterol fumarate.

20. The method of claim 14, wherein the second solution comprises formoterol fumarate dihydrate.

21. The method of claim 20, wherein the second solution comprises from about 0.0025 to about 0.32 mg/mL of formoterol fumarate dihydrate.

22. The method of claim 14, wherein each of the first solution and the second solution comprises from about 2 to about 10 mg/mL of sodium chloride.

23. The method of claim 14, wherein each of the first solution and the second solution comprises about 9 mg/mL of sodium chloride.

24. The method of claim 14, wherein the first solution and/or the second solution further comprises sodium citrate, citric acid, or any combination thereof.

25. The method of claim 14, wherein the first solution and/or the second solution comprises sodium citrate and citric acid.

26. The method of claim 14, wherein the first solution and/or the second solution further comprises edetate disodium.

27. The method of claim 14, wherein the first solution and/or the second solution further comprises hydrochloric acid, sodium hydroxide, or any combination thereof.

28. The method of claim 14, wherein the volume of each of the first and second solutions is about 0.5 to about 5 mL.

29. A method of administering tiotropium and formoterol to a patient in need thereof comprising administering to the patient by inhalation with a nebulizer a first solution of tiotropium or a pharmaceutically acceptable salt thereof and a second solution of formoterol or a pharmaceutically acceptable salt thereof, wherein the first solution comprises about 9 mg/mL of sodium chloride and the second solution comprises about 5 mg/mL of sodium chloride.

30. A method of administering tiotropium and formoterol to a patient in need thereof comprising administering to the patient by inhalation with a nebulizer a first solution of tiotropium or a pharmaceutically acceptable salt thereof and a second solution of formoterol or a pharmaceutically acceptable salt thereof, wherein the first solution and/or the second solution comprises from about 0.001 to about 1 mg/mL of edetate disodium.

* * * * *